United States Patent
Ganio

(10) Patent No.: US 11,850,259 B2
(45) Date of Patent: Dec. 26, 2023

(54) METHODS OF TREATING VIRAL INFECTIONS AFFECTING THE RESPIRATORY TRACT USING TOPICALLY ADMINISTERED LITHIUM AGENTS

(71) Applicant: United States Government as Represented by the Department of Veterans Affairs, Washington, DC (US)

(72) Inventor: Carl Ganio, Wilmington, NC (US)

(73) Assignee: THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 249 days.

(21) Appl. No.: 17/494,230

(22) Filed: Oct. 5, 2021

(65) Prior Publication Data
US 2022/0105128 A1    Apr. 7, 2022

Related U.S. Application Data

(60) Provisional application No. 63/198,228, filed on Oct. 5, 2020.

(51) Int. Cl.
*A61K 33/14*   (2006.01)
*A61P 37/02*   (2006.01)
*A61K 9/00*    (2006.01)
*A61K 45/06*   (2006.01)

(52) U.S. Cl.
CPC ............ *A61K 33/14* (2013.01); *A61K 9/0073* (2013.01); *A61K 45/06* (2013.01); *A61P 37/02* (2018.01)

(58) Field of Classification Search
None
See application file for complete search history.

(56) References Cited

U.S. PATENT DOCUMENTS

| | | |
|---|---|---|
| 2009/0068253 A1 | 3/2009 | Guilford |
| 2012/0244212 A1 | 9/2012 | Guilford |
| 2016/0151438 A1 | 6/2016 | Truscott et al. |
| 2016/0310524 A1 | 10/2016 | Ankenman |
| 2016/0375052 A1 | 12/2016 | Idelevich et al. |
| 2023/0181556 A1* | 6/2023 | Villoutreix ........... A61K 31/496 514/290 |

FOREIGN PATENT DOCUMENTS

| | | | |
|---|---|---|---|
| WO | WO 2000016625 A1 * | 3/2000 | ............ A01N 43/04 |
| WO | 2017/215591 A1 | 12/2017 | |
| WO | 2012/125941 A1 | 9/2021 | |

OTHER PUBLICATIONS

Minashima, et al. (2014) "Lithium Protects Against Cartilage Degradation in Osteoarthritis," Arthritis Rheumatol, vol. 66 (5) pp. 1228-1236.
Gao, et al. (2013) "Inhibition of Glycogen Synthase Kinase 3beta Activity with Lithium Prevents and Attenuates Paclitaxel-Induced Neuropathic Pain," Neuroscience vol. 254, pp. 301-311.
Weinsanto, et al. (2018) "Lithium Reverses Mechanical Allodynia Through a mu Opioid-Dependant Mechanism;" Molecular Pain, vol. 14, pp. 1-8.
Banafshe, et al. (2012) "Lithium Attenuates Pain-Related Behavior in Rat Model of Neuropathic Pain: Possible Involvement of Opioid System" Pharmacology, BioChemistry, and Behavior vol. 100 pp. 425-430.
Harrison, et al. (2007) "Lithium Chloride Inhibits the Coronavirus Infectious Bronchitis Virus in Cell Culture," Avian Pathology, vol. 36:2 pp. 109-114.
Chang (2004) "Induction of IL-8 Release in Lung Cells via Activator Protein-1 by Recombinant Baculovirus Displaying Severe Acute Respiratory Syndrome-Coronavirus Spike Proteins: Identification of Two Functional Regions," j immunol, vol. 173 pp. 7602-7614.
Puthothu, et al. (2006) "Impact of IL8 and IL8-Receptor Alpha Polymorphisms on the Genetics of Bronchial Asthma and Severe RSV Infections" Clin Mol Allergy, vol. 4:2.
Versteeg, et al. (2007) "The Coronavirus Spike Protein Induces Endoplasmic Reticulum Stress and Upregulation of Intracellular Chemokine mRNA Concentrations," Journal of Virology, vol. 81: 20 pp. 10981-10990.
Spuch, et al. (2020) "Does Lithium Deserve a Place in the Treatment Against COVID-19 a Preliminary Observational Study in Six Patients, Case Report," Front Pharmacol, vol. 11, Article 557629, 8 pgs.

* cited by examiner

*Primary Examiner* — Brian J Davis
(74) *Attorney, Agent, or Firm* — Ballard Spahr LLP

(57) ABSTRACT

This disclosure relates to topical lithium agents including inhalable lithium agents for treating a viral infection characterized by a cytokine storm in the respiratory tract of a subject such as a human. Topical lithium formulations can be used to mitigate such viral infections, including coronavirus infections.

17 Claims, 8 Drawing Sheets

METHODS OF TREATING VIRAL INFECTIONS AFFECTING THE RESPIRATORY TRACT USING TOPICALLY ADMINISTERED LITHIUM AGENTS

CROSS REFERENCE TO RELATED APPLICATIONS

This application claims priority to U.S. Provisional Application No. 63/198,228, filed Oct. 5, 2020, the entirety of which is incorporated into this application by reference.

BACKGROUND

Severe acute respiratory syndrome coronavirus-2 (SARS-CoV-2) is a new type of coronavirus that affects the respiratory system. The virus was responsible for the COVID-19 pandemic, which has and continues to be a major threat to healthcare systems and economies worldwide. Despite the availability of vaccines, there continues to be a need for SARS-CoV-2 therapies as well as therapies effective at treating other viruses affecting the respiratory tract through similar mechanisms. These needs and others are satisfied by the following disclosure.

SUMMARY

This disclosure relates to topical (e.g., inhalable) lithium agents for treating a viral infection characterized by a cytokine storm in the respiratory tract of a subject such as a human. Topical lithium formulations can be used to mitigate such viral infections, including coronavirus infections. Without being bound by any theory, topical lithium agents can be used to modulate protein kinase signaling cascades and other events associated with the cytokine storm, including recruitment of IL-8 and leucocyte/monocyte recruitment. Administration of topical lithium agents can also result in a protective anti-apoptotic effect on cellular death.

According to one embodiment, the method of treating a viral infection characterized by a cytokine storm in the respiratory tract of a subject involves administering to the subject topically to the respiratory tract a therapeutically effective amount of a lithium agent.

According to a further embodiment, a disclosed kit can comprise a topical form of a lithium agent, the topical form comprising a therapeutically effective amount of a lithium agent for treating a viral infection characterized by a cytokine storm in the respiratory tract of a subject; together with one or more of the following: zinc, a non-steroidal anti-inflammatory agent, an antibiotic, azithromycin, an antiviral medication, a neuraminidase inhibitor, hydroxychloriquine, chloriquine, a histamine 2 receptor antagonist, a steroid, or Vitamin C.

BRIEF DESCRIPTION OF THE DRAWINGS

The foregoing summary, as well as the following description of the disclosure, is better understood when read in conjunction with the appended drawings. For the purpose of illustrating the disclosure, the drawings illustrate some, but not all, alternative embodiments. This disclosure is not limited to the precise arrangements and instrumentalities shown. The following figures, which are incorporated into and constitute part of the specification, assist in explaining the principles of the disclosure.

DETAILED DESCRIPTION

Figure 1A:
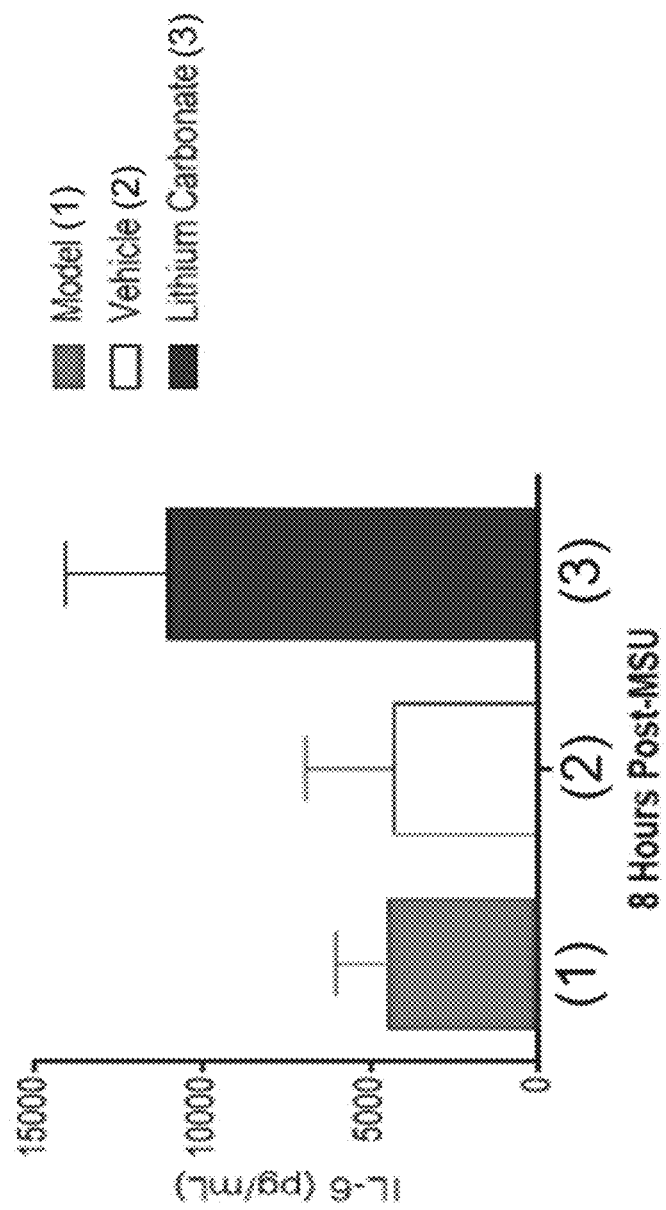
FIG. 1A is a bar graph showing levels of IL-6 (pg/mL) eight hours post monosodium urate (MSU)-induced gout in the rat ankle for model (1), vehicle (2), and topical lithium carbonate treatments.

The present disclosure provides for methods and kits of using topical lithium formulations to treat infection and symptoms caused by viruses characterized by a cytokine storm in the respiratory tract of a subject, including Severe Acute Respiratory Syndrome Coronavirus 2 (SARS-CoV-2) and other pathogenic microbial organisms that affect the respiratory tract. The methods of using topical lithium agents can also be used to prevent or treat bronchiolitis, asthma, RSV, influenza, cystic fibrosis, chronic obstructive pulmonary disease, and pulmonary fibrosis.

A. DEFINITIONS

When the term "about" precedes a numerical value, the numerical value can vary within ±10% unless specified otherwise.

"Subject" means any subject, including mammalian subjects such as humans. In some specific embodiments, the human subject can be classified as high risk for coronavirus complications, e.g., an adult aged 65 or older, an adult with high blood pressure, asthma, lung disease, diabetes, heart disease, kidney disease, lung disease, cancer, or an immunocompromised adult or child. In some further specific embodiments, the subject is an infant, and in some cases, a premature infant.

"Respiratory tract" means the respiratory organ system responsible for the exchange of oxygen and carbon dioxide which, in humans, spans from the nostrils to the lung alveoli. The respiratory tract is divided into the upper respiratory tract (URT) and the lower respiratory tract (LRT). The URT includes the nose, nasal passages, paranasal sinuses, the nasopharynx and oropharynx and the portion of the larynx above the vocal cords. The LRT includes the portion of the larynx below the vocal cords, the trachea, smaller airways (that is, bronchi and bronchioli) and alveolar ducts, alveolar sacs and alveoli.

"Treating" or "treatment" means improving, reducing, or alleviating at least one symptom or biological consequence of the infection in a subject, including reducing or decreasing virus titer, load, replication or proliferation in a subject following exposure to the virus. The term also includes shortening the time period during which a subject exhibits at least one symptom or biological consequence of virus infection after being infected by a virus. The subject can exhibit or be diagnosed with one or more symptoms or biological consequences of virus infection. In the context of viral infections characterized by a cytokine storm in the respiratory tract, "treatment" includes 1) inhibition of the replication of viruses, including SARS-CoV-2 virus, 2) increasing the immune response by reducing lymphopenia, and 3) reducing inflammation by preventing or reducing the cytokine storm.

"Therapeutically effective amount" means an amount of a composition or formulation sufficient to improve the condition being treated or achieve the desired benefit.

"Cytokine storm" has its recognized meaning in the art, i.e., an event in which various inflammatory cytokines are produced at a much higher rate than normal. The overproduction of cytokines can cause unwanted feedback on other immune cells, in turn allowing for progressive worsening of viral infections characterized by a cytokine storm.

The "viral infection" can be due to any virus characterized by a cytokine storm, including those viruses belonging to the Coronaviridae family, whether known or yet to be discovered. Exemplary coronaviruses include 229E (alpha coronavirus), NL63 (alpha coronavirus), OC43 (beta coronavirus), HKU1 (beta coronavirus), MERS-CoV (the beta coronavirus associated with Middle East Respiratory Syndrome, or MERS), SARS-CoV (the beta coronavirus associated with severe acute respiratory syndrome, or SARS) and SARS-CoV-2 (the novel coronavirus associated with coronavirus disease 2019, or COVID-19). Other examples include the Human orthopneumovirus (also known as human respiratory syncytial virus, or HRSV, or RSV).

B. TREATMENT METHODS AND KITS

As disclosed in PCT/US2020/038736, the contents of which are incorporated by reference, formulations including a lithium agent can be used for the prevention and treatment of inflammatory conditions such as gout, joint disease and pain, and symptoms thereof. Such conditions involve a cytokine attack similar to the attack that occurs with certain viruses, including SARS-Cov-2 and others. The cytokine storm seen in COVID-19 involves the lung tissue. This contributes to the majority of fatalities and routinely necessitates ventilator support. The severity and outcomes associated with COVID-19 infections can be directly related to circulating (and local) levels of IL-8, among other substances associated with the cytokine storm.

A downside of using oral lithium agents for any condition is that it can be toxic, and blood levels of lithium must be routinely monitored. As a result, this disclosures relates to topical lithium agents, i.e., topical application of the lithium agent directly to the respiratory tract, to deliver the therapeutic agent directly to the affected area. The method can be useful for treating a viral infection caused by a virus belonging to the Coronaviridae family, such as Severe Acute Respiratory Syndrome Coronavirus 2 (SARS-CoV-2). Other viral infections that can be treated include those caused by Human orthopneumovirus.

In some embodiments, the lithium agent can be in any suitable chemical or elemental form of a lithium agent, including elemental lithium, lithium acetate, lithium aluminate, lithium aluminum hydride, lithium amide, lithium aspartate, lithium azide, lithium beryllide, lithium bis(trifluoromethanesulfonyl)imide, lithium bis(trimethylsilyl)amide, lithium borate, lithium borohydride, lithium bromide, lithium carbide, lithium carbonate, lithium chlorate, lithium chloride, lithium citrate, lithium cobalt oxide, lithium cyanide, lithium diisopropylamide, lithium disilicate, lithium fluoride, lithium hexafluorogermanate, lithium hexafluorophosphate, lithium hydride, lithium hydroxide, lithium hypochlorite, lithium imide, lithium iodate, lithium iodide, lithium iridate, lithium iron phosphate, lithium lactate, lithium metaborate, lithium metasilicate, lithium methoxide, lithium molybdate, lithium molybdenum purple bronze, lithium monoxide anion, lithium nickel cobalt aluminum oxides, lithium nickel manganese cobalt oxides, lithium niobate, lithium nitrate, lithium nitride, lithium nitrite, lithium orotate, lithium orthosilicate, lithium oxide, lithium perchlorate, lithium peroxide, lithium platinate, lithium polonide, lithium ruthenate, lithium salicylate, lithium selenide, lithium stearate, lithium succinate, lithium sulfate, lithium sulfide, lithium sulfite, lithium superoxide, lithium tantalate, lithium tetrachloroaluminate, lithium tetrafluoroborate, lithium tetrahydridogallate, lithium tetrakis(pentafluorophenyl)borate, lithium tetramethylpiperidide, lithium titanate, lithium triborate, lithium triethylborohydride, lithium triflate or lithium tungstate. In some embodiments, lithium is lithium carbonate, lithium citrate, lithium salicylate, or lithium lactate. In one embodiment, the lithium is lithium carbonate.

The route of administering can include any topical route of administration. In some embodiments, routes of administration include nasal inhalation, oral inhalation, and nasal delivery through administration to the nasal epithelium. In particular embodiments, routes of administration include nasal, inhalational, intratracheal, intrapulmonary, and intrabronchial administration. Dosage forms include, for example, dispersions, suspensions, powders, liquid sprays for nasal or oral inhalation, dry powder or aerosolized formulations for inhalation, and the like. In some embodiments, the course of treatment can be less than two weeks, e.g., 1, 2, 3, 4, 5, 6, 7, 8, 9, 10, 11, 12, 13 or 14 days. Toxicity levels of lithium can be monitored during treatment.

In particular embodiments, the lithium agent is administered by nebulizer, inhaler, foam, mist, positive pressure ventilation, endotracheal tube, gel, or other suitable vehicle directly to lung tissue or into the bronchial tree. In such cases, the epithelium or localized vasculature is directly affected. In particular embodiments, alveolar structures are subjected to the lithium agent to stop anti-inflammatory reactions and infiltration from the endothelium into the lung tissue.

In some embodiments, the lithium agent can be inhaled in aerosolized form (including particles or droplets having a diameter of generally less than 10 μm). Carrier liquids and powders that are suitable for inhalation are commonly used in traditional asthma inhalation therapeutics, and thus are well known in the art. The optimal dosage range can be determined by routine procedures by a pharmacologist of ordinary skill in the art. When the lithium agent is inhaled in solid or liquid form, the particles or droplets can be deposited throughout the respiratory system, with larger particles or droplets tending to be deposited near the point of entry (i.e., in the mouth or nose) and smaller particles or droplets being carried progressively further into the respiratory system before being deposited in the trachea, bronchi, and finally the alveoli.

In some embodiments, a particle/droplet diameter of 10 microns or less can be used. Determination of the preferred carrier (if any), propellant (which can include the lithium agent diluted in an inert gas such as nitrogen for example), design of the inhaler, and formulation of the lithium in its carrier are within the ordinary skill in the art. A portable inhaler can contain the lithium agent either mixed in dry form with a propellant or held in a chamber separate from the propellant, or mixed with a liquid carrier capable of being nebulized to an appropriate droplet size, or in any other configuration known to those skilled in inhaler technology.

In certain embodiments, in addition to the lithium agent, the formulations can include at least one adjuvant such as a penetration enhancer, anti-oxidant, stabilizer, carrier, or vehicle. In some embodiments, the compositions including the lithium agent and the pharmaceutically acceptable carrier can contain about 0.001% to about 99.9% by weight lithium agent, in some embodiments, 0.01 wt. % to 90 wt. % lithium agent, 1 wt. % to about 80.0 wt. %, 1 wt. % to about 50.0 wt. %, or about 1 wt. % to about 30 wt. % lithium agent, with the remainder of the composition including a pharmaceutically acceptable carrier or an additional therapeutic agent for the treatment of the viral infection. The carrier can be any pharmaceutically acceptable material, composition or carrier, such as a liquid or solid filler, stabilizer, dispersing agent, suspending agent, diluent, excipient, thickening agent, or solvent or encapsulating material.

In further embodiments, the method can include concomitant administration to the subject of an effective amount of a respiratory disorder agent along with administration of the composition including the lithium agent in a pharmaceutically acceptable carrier. In particular embodiments, the lithium agent can be administered concomitantly with any therapeutic agent used to treat a respiratory disorder, including SARS-Cov-2, COVID-19, RSV, influenza, asthma, bronchiolitis, cystic fibrosis, chronic obstructive pulmonary disease and/or pulmonary fibrosis and symptoms thereof. In some embodiments, the therapeutic agent includes zinc, a non-steroidal anti-inflammatory drug (NSAID; e.g., aspirin, diclofenac, ibuprofen, indomethacin, ketoprofen, ketorolac, naproxen, etc.), antibiotics, azithromycin, antiviral medications, a neuraminidase inhibitor, hydroxychloroquine, chloroquine, histamine 2 receptor antagonists (e.g. famotidine), steroid treatment (e.g., dexamethasone), or Vitamin C.

In further embodiments, administration of the lithium agent can be provided in combination with supportive care, including oxygen therapy or supplemental oxygen, continuous positive airway pressure (CPAP) or heated humidified high-flow (HHHF) therapy, high flow nasal cannulae (HFNC) or high flow nasal oxygen (HFNO).

Also disclosed are kits or an assembly of components packaged together or separately with optional instructions (written, audio, or visual) regarding how to use the components of the kit. The kits can include a topical form of a lithium agent such as inhalable lithium, together with one or more agents that can be useful for treating a viral infection characterized by the cytokine storm. The kit can include packaging materials that can maintain the components and can be composed of material commonly used for such purposes (e.g., paper, corrugated fiber, glass, plastic, foil, ampules, vials, tubes, bottles, syringes, etc.).

C. EXAMPLES

The following examples further illustrate this disclosure. The scope of the disclosure and claims is not limited by the scope of the following examples.

The following study involved the topical application of 2% lithium carbonate in a monosodium urate (MSU)-induced model of gout in the rat ankle. Because topical application of lithium attenuated gout in the study, and the cytokine storm associated with gout is analogous to the cytokine storm associated with viral infections affecting the respiratory attack, the study demonstrates the efficacy of topical lithium in attenuating the cytokine storm associated with viral infections such as SARs-CoV-2 among others.

Figure 1B:
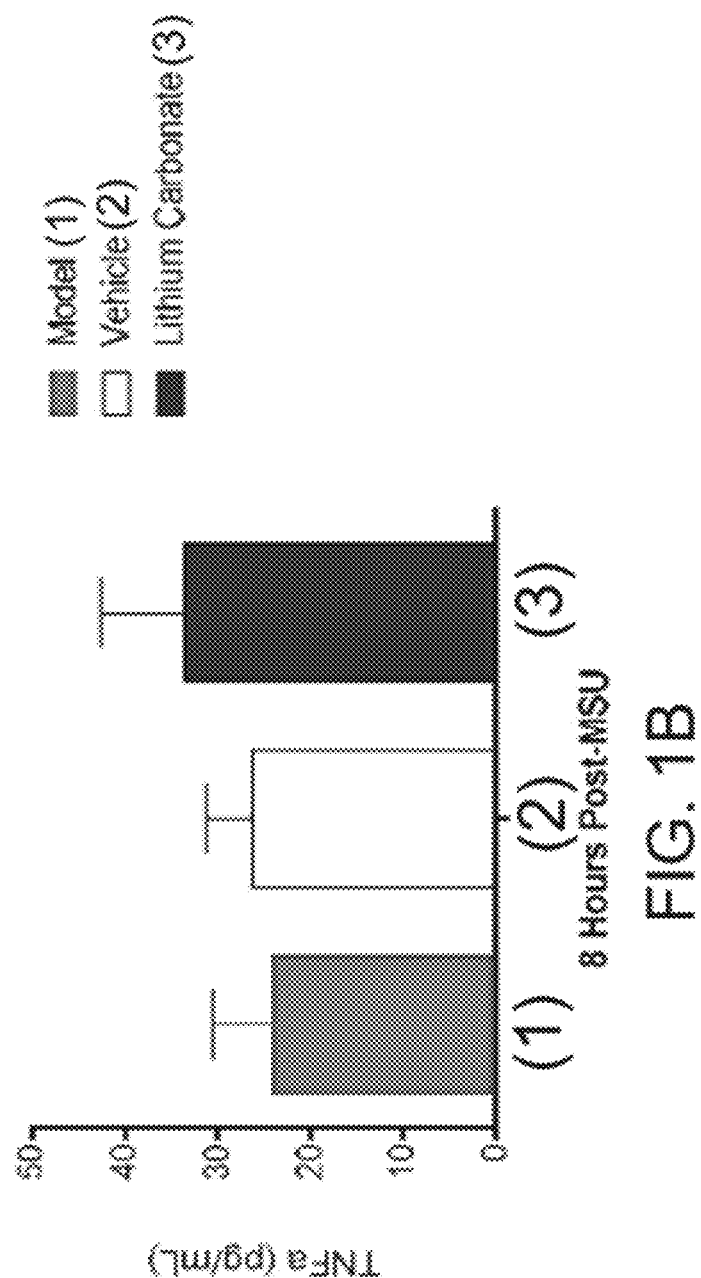
FIG. 1B is a bar graph showing levels of TNF-α (pg/mL) eight hours post MSU-induced gout in the rat ankle for model (1), vehicle (2), and topical lithium carbonate treatments.
Figure 1C:
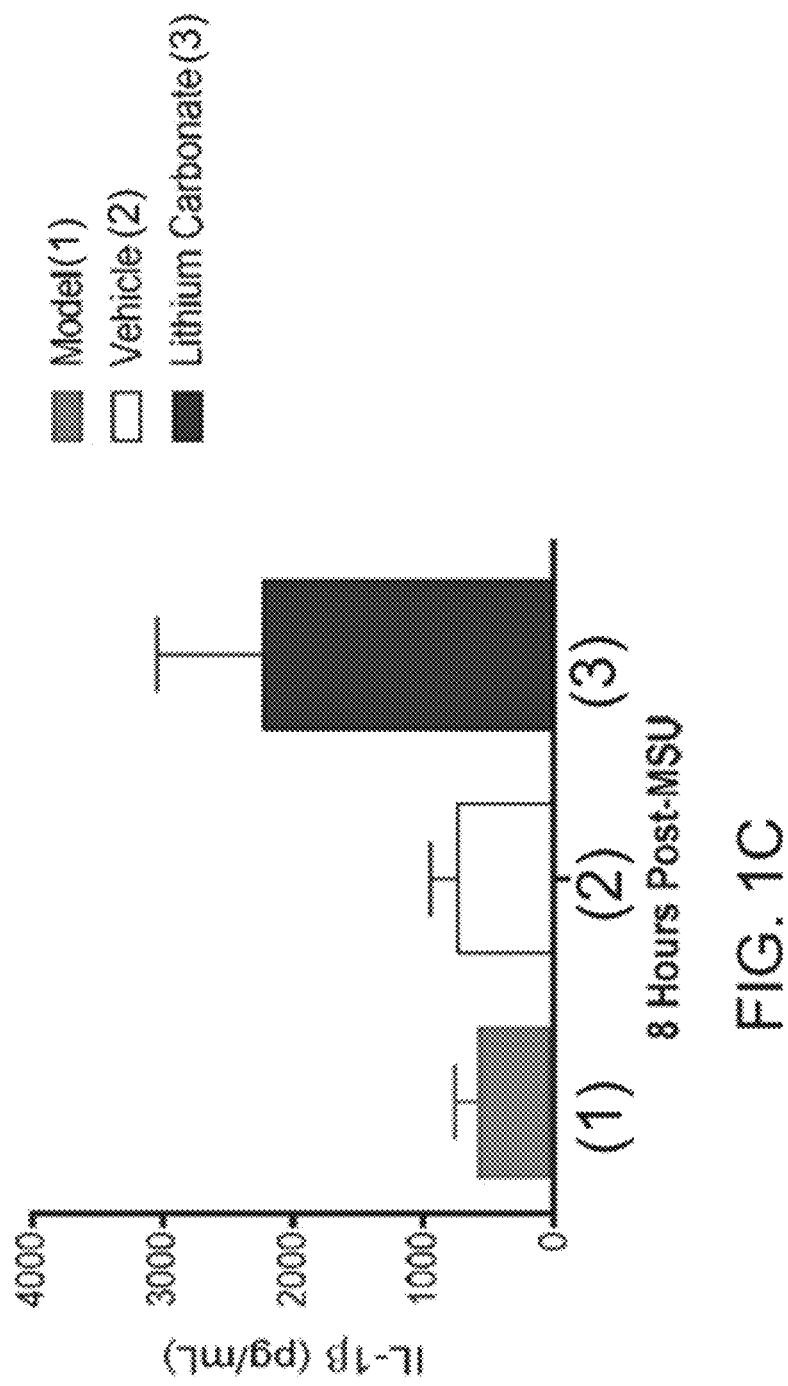
FIG. 1C is a bar graph showing levels of IL-1β (pg/mL) eight hours post MSU-induced gout in the rat ankle for model (1), vehicle (2), and topical lithium carbonate treatments.

The basis of the study was to initiate a gouty attack in a rat ankle via injection of MSU (monosodium urate) crystals. Standard inflammatory markers IL-1β, IL-6, and TNF-α were measured. The results showed an increase in IL-1 (3, IL-6, and TNF-α. The elevation of these cytokines would be expected as a normal inflammatory response to MSU injected into the rat ankle. The anticipated gouty flare was initiated for application of the DMSO vehicle and lithium carbonate for clinical studies (see FIGS. 1A-1C).

The inhibition of GSK3B by lithium carbonate increased the TNF-α protein synthesis by greater than a 3-fold margin in neutrophils. Lithium led to a consistent increase of IL-1β, IL-6 and TNF-α in the serum of subjects tested. Under certain experimental conditions lithium also exhibits other pro-inflammatory properties, e.g., induction of IL-4, IL-6 and other pro-inflammatory cytokines' synthesis. While not bound by any theory, the "priming" of the inflammatory response, and induction of cytokines IL-1β, IL-6, and TNF-α in the BRT model can be attributed to the topical lithium carbonate applied.

Figure 2:
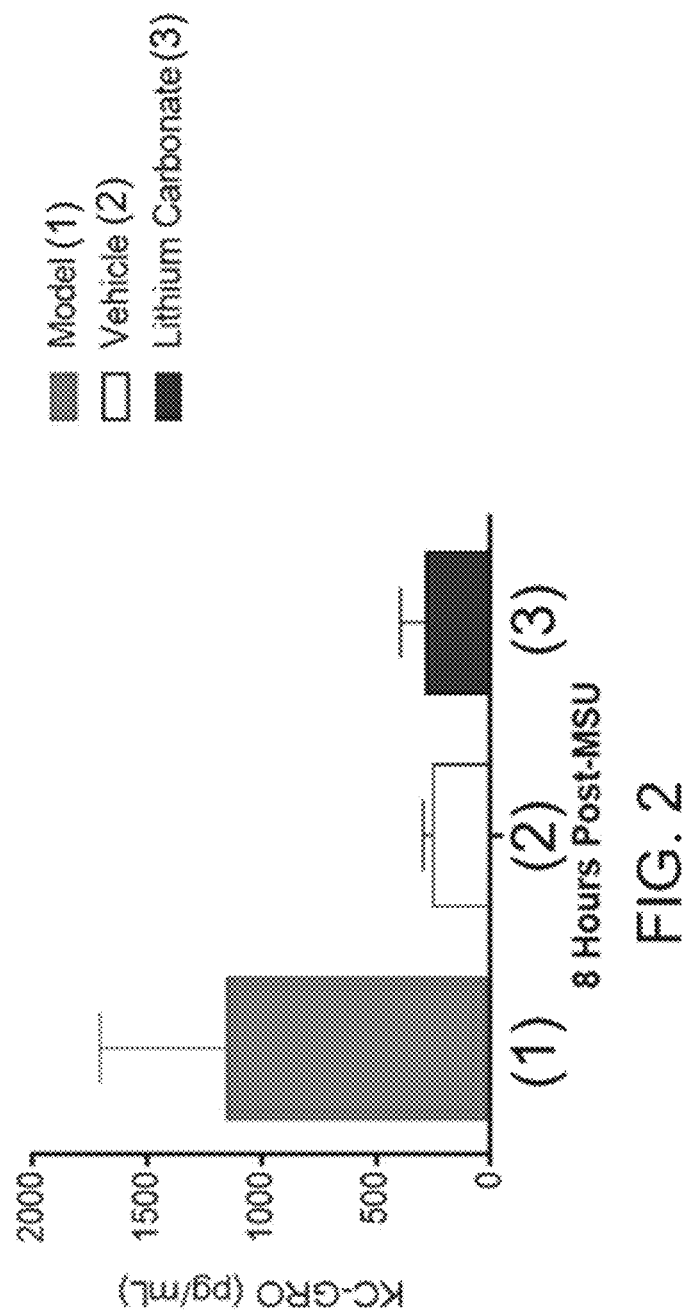
FIG. 2 is a bar graph showing levels of KC-GRO (pg/mL) eight hours post MSU)-induced gout in the rat ankle for model (1), vehicle (2), and topical lithium carbonate treatments.

Another chemokine surprisingly showed activity in the model. This chemokine was KC-GRO; and although present at a lower level, it was included in the panel for measurement in the study. The chemokine KC-GRO is the murine equivalent of IL-8 (CXCL8) in the human. It is essential for neutrophil recruitment into the synovium. This is a hallmark of a gout attack and can be considered a cytokine storm within and around the affected joint—similar to the cytokine storm seen with viruses affecting the respiratory tract such as SARs-CoV-2 among others. KC-GRO was surprisingly lessened by topical application of lithium as shown in FIG. 2.

Attenuation of cytokine KC/GRO was seen in synovial fluid with application of a topical lithium carbonate as the test ingredient in the BRT rat MSU model. This was a surprising and unexpected finding in light of the increase in the other cytokines that were tested. Previous studies have established that KC is the murine homologue of human GRO-a; the KC receptor is also an IL-8 receptor homologue capable of binding both KC and the macrophage inflammatory protein-2 with high affinity. The interaction of KC/GRO (as it binds the IL-8 receptor) triggers neutrophil activity. Rapid release of IL-8 and binding to CXCL2 stimulate the adhesion and diapedesis of neutrophils out of the endothelium into the synovium. The CXCL1/CXCL2 interaction is also known to regulate and activate the NLRP3 inflammasome in macrophages. The neuronal inflammatory cytokines CXCL1/CXCL2 are regulated by GSK3 signaling.

The cytokine CXCL1 that binds the human IL-8, and its receptor CXCL-2, are essential for the development of the acute gouty neutrophilic response to urate crystals in the murine gout subcutaneous air pouch model. In a resting state, neutrophils are rare in synovial fluid. The CXC chemokine IL-8 in one previous study accounted for more than 90% of the neutrophil chemotactic activity seen. The IL-8 acts on CXCL1/CXCL2 to recruit neutrophils out of the endothelium.

Figure 3:
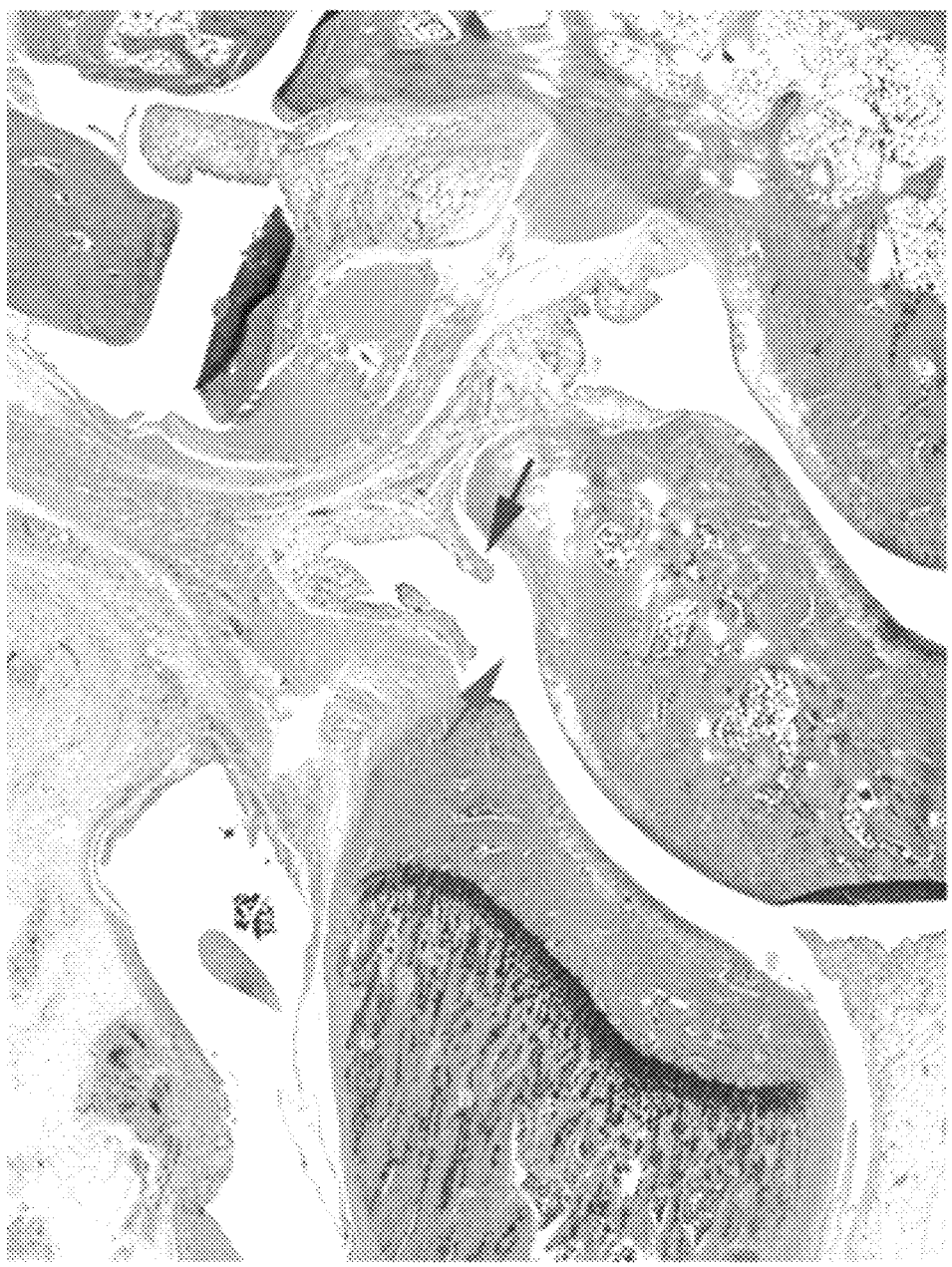
FIG. 3 shows a photomicrograph of a normal joint free of edema or inflammatory infiltrates.
Figure 4:
FIG. 4 shows a photomicrograph after a gouty attack, demonstrating neutrophil recruitment from capillaries and infiltration into the joint. As can be seen from the photomicrograph, the joint space is swollen with edema, and rafts of neutrophils and hypertrophy of synoviocytes are evident.
Figure 5:
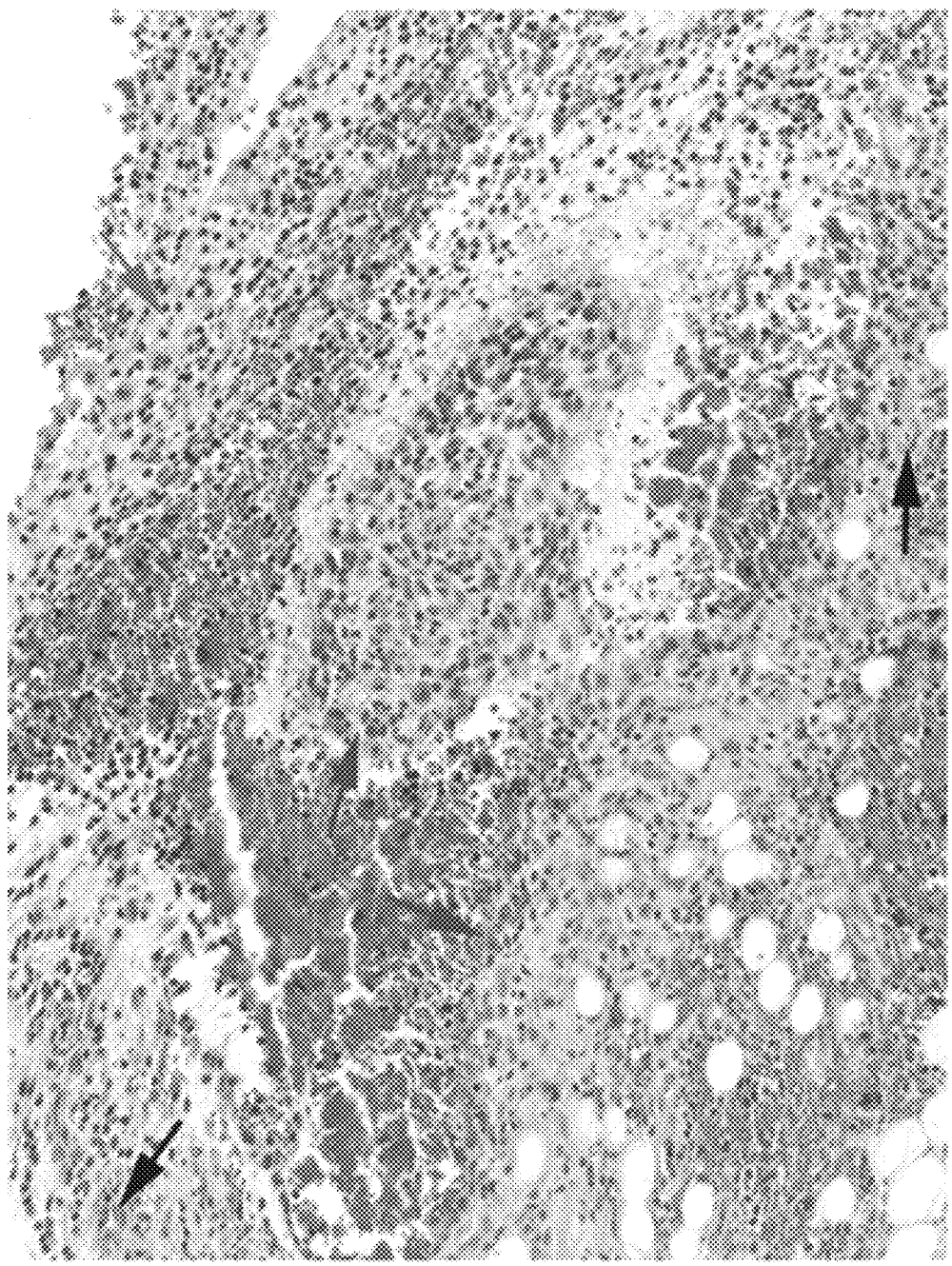
FIG. 5 shows the photomicrograph of FIG. 4 after a gouty attack, amplified at 20 times magnification.
Figure 6:
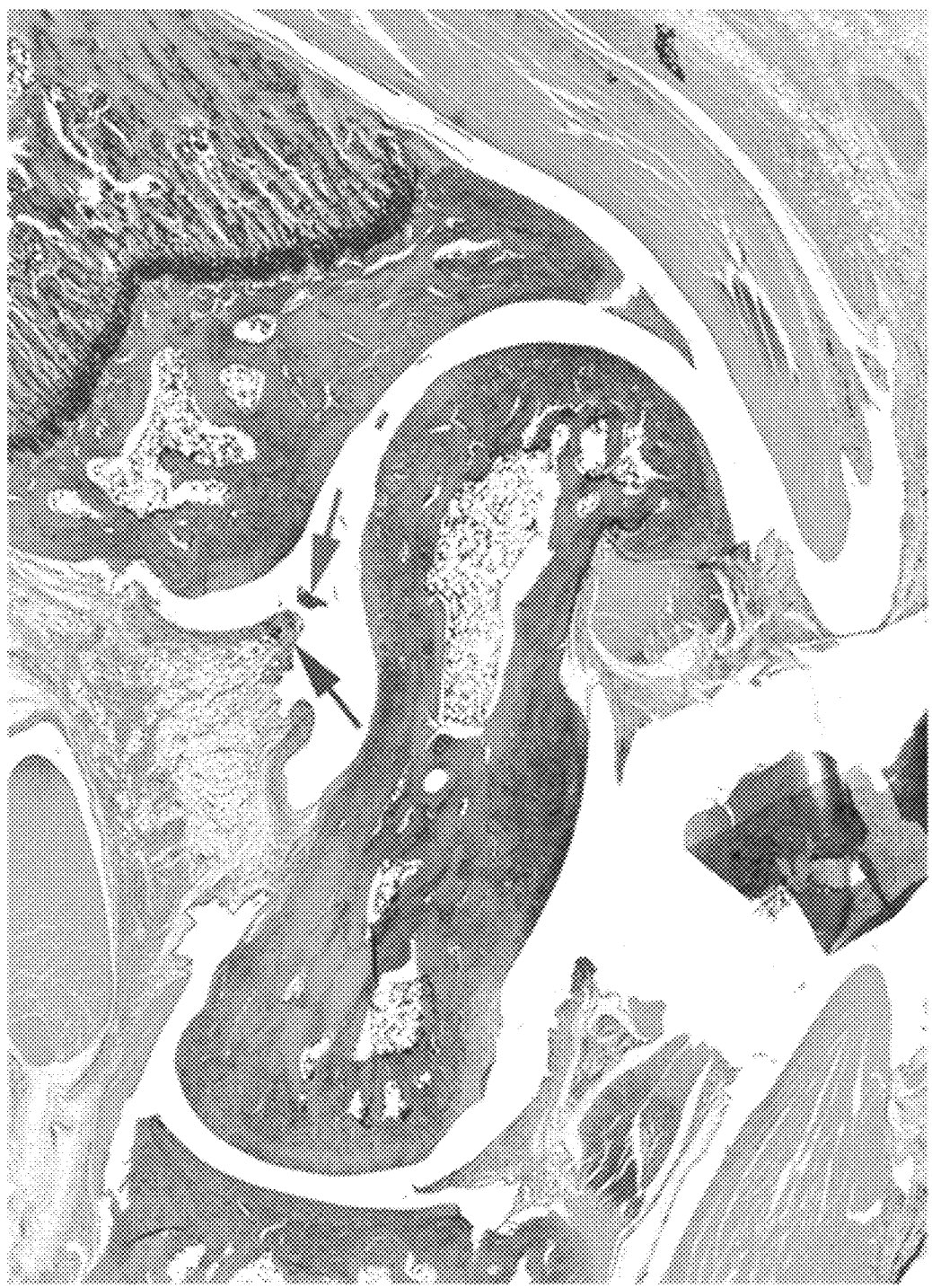
FIG. 6 shows a photomicrograph at 2-times magnification after the topical administration of lithium carbonate. Topical application of lithium carbonate produced surprising changes. There was minimal synovial hypertrophy, minimal edema, and only a very small raft of white blood cells.

It was anticipated that the pathology may bring additional clarity to show lithium carbonate's action on the cytokine storm. Rat ankle samples banked in formalin were sent for microscopic analysis. FIG. 3 shows a photomicrograph of a normal joint free of edema or inflammatory infiltrates. As shown in FIG. 4, the gouty attack is marked by neutrophil recruitment from capillaries and infiltration into the joint. The joint space is swollen with edema, and rafts of neutrophils and hypertrophy of synoviocytes are seen. As shown in FIG. 5 at 20-times magnification, there was a massive infiltration of neutrophils and fibrin free within the joint cavity. The "raft" of white blood cells was large. The capillary endothelium was hypertrophied, suggestive of increased vascular permeability or leakiness. As shown in FIG. 6 at 2-times magnification, topical application of lithium carbonate produced surprising changes. There was minimal synovial hypertrophy, minimal edema, and only a very small raft of white blood cells.

The analogy of KC-GRO to human IL-8 is known. The cytokine storm of gout is analogous to the cytokine storm of that seen with respiratory illnesses include SAR-CoV-2 and COVID-19. Results seen with topical application of lithium to the epithelium in gouty synovial edema and concomitant white blood cell recruitment provide a basis for topically applying (e.g., by inhalation) lithium to the lung tissue for respiratory illnesses such as SARS-CoV-2. Topical application of lithium to accessible targeted tissues can achieve the desired effect with less of the negative systemic side effects. The potential for lithium to reduce IL-8 and reduce the influx of white blood cells is believed capable of attenuating the cytokine storm and thereby mitigating the most damaging effects of SARS-CoV-2 and other respiratory illnesses on the lungs.

In the gout model, lithium was applied to the epithelium of the skin, and penetrated to the synovium. Once that occurred, the lithium acted on the tissues and blood vessels surrounding the joint, preventing the entry of the inflammatory cells into the joint. Thus, lithium ions were able to penetrate the epithelium of the skin which is more more stratified and keratinized, and presents a greater barrier to penetration, relative to lung tissue. While the cells of the alveoli are epithelium, they are not thick and keratinized, and thus present less of a barrier to penetration of lithium. Thus, penetration should be immediate. This allows for attenuation of IL-8 and the mitigation of inflammatory cells that produce inflammatory infiltrates of cells and edema into the lungs.

Additional details regarding the gout study can be found in "Topical Application of 2% Lithium Carbonate Reduces Pain, Swelling and the Chemokind KC-GRO (Murine IL-8) in a MSU-Induced Model of Gout in the Rat Ankle," *Journal of Cytokine Biology*, Vol. 6, Issue 1, (2021). The entirety of this publication is incorporated by reference for its teachings demonstrating the anti-inflammatory effects of topical lithium and the effect of lithium in attenuating the cytokine storm associated inflammatory responses such as gout. Further details can be found in PCT/US2020/038736 (published as WO 2020/257650), the entirety of which is incorporated by reference for its teachings of topical administration of lithium to treat cytokine storms associated with inflammatory conditions such as gout.

D. REFERENCES

Ganio, Carl "Topical Application of 2% Lithium Carbonate Reduces Pain, Swelling and the Chemokine KC-GRO (Murine IL-8) in a MSU-induced Model of Gout in Rat Ankle. Journal of Cytokine Biology 2021, 6:1.

Giambelluca, Miriam S., et al. "TNF-α Expression in Neutrophils and its Regulation by Glycogen Synthetase Kinase-3: A Potentiating Role for Lithium." *The FASEB Journal,* 28, 3679-3690 (2014) www.fasebj.org.

Petersein, Charlotte, et al. "Impact of Lithium Alone and in combination with Antidepressants on Cytokine Production in Vitro." *Journal of Neural Transmission*, Accepted Oct. 20, 2014 DOI: 10.1007/s00702-014-1328-6.

Nassar, Ahmad, and Abed N. Azab. "Effects of Lithium on Inflammation." *ACS Chemical Neuroscience*, vol. 5, no. 6, 2014, pp. 451-458, doi:10.1021/cn500038f.

Bozic, C. R., et al. "The Murine Interleukin 8 Type B Receptor Homologue and Its Ligands." *The Journal of Biological Chemistry*, Vol. 269, N. 47, Nov. 25, 1994, pp. 29355-29358.

Boro, M., and Balaji, K. N. "CXCL1 and CXCL2 Regulate NLRP3 Inflammasome Activation via G-protein-Coupled Receptor CXCR2." *The Journal of Immunology*, Jun. 21, 2017. www.jimmunol org/cgi/doi/10.4049/jimmunol.1700129.

Chai, H., et al. "The Cytokine CXCL1 and Its Receptor CXCR2 Contribute to Chronic Stress-Induced Depression in Mice." *FASEB Journal*, Volume 33, Apr. 29, 2020 pp. 8853-8864 doi: 10.1096/fj.201802359RR.

Terkektaub, R., et al. "The Murine Homolog of the Interleukin-8 Receptor CXCR-2 is Essential for the Occurrence of Neutrophilic Inflammation in the Air Pouch Model of Acute Urate Crystal-Induced Gouty Synovitis." *Arthritis and Rheumatism*, Vol. 41, No. 5, May 1998, pp. 900-909.

Girbl, Tamara, et al. "Distinct Compartmentalization of the Chemokines CXCL1 and CXCL2 and the Atypical Receptor ACKR1 Determine Discrete Stages of Neutrophil Diapedesis." *Immunity,* 201.8; 49, pp. 1062-1076. https://doi.org/10.1016/j.immuni.0.2018.09.018.

What is claimed is:

1. A method of treating a viral infection characterized by a cytokine storm in the respiratory tract of a subject, the method comprising topically administering to the subject's respiratory tract a therapeutically effective amount of a lithium agent.

2. The method of claim 1, wherein topical administration comprises inhalation.

3. The method of claim 1, wherein the lithium agent is not administered orally.

4. The method of claim 1, wherein the viral infection is caused by a virus belonging to the Coronaviridae family.

5. The method of claim 1, wherein the viral infection is caused by Severe Acute Respiratory Syndrome Coronavirus 2 (SARS-CoV-2) or Human orthopneumovirus.

6. The method of claim 1, wherein the the lithium agent is elemental lithium, lithium acetate, lithium aluminate, lithium aluminum hydride, lithium amide, lithium aspartate, lithium azide, lithium beryllide, lithium bis(trifluoromethanesulfonyl)imide, lithium bis(trimethylsilyl)amide, lithium borate, lithium borohydride, lithium bromide, lithium carbide, lithium carbonate, lithium chlorate, lithium chloride, lithium citrate, lithium cobalt oxide, lithium cyanide, lithium diisopropylamide, lithium disilicate, lithium fluoride, lithium hexafluorogermanate, lithium hexafluorophosphate, lithium hydride, lithium hydroxide, lithium hypochlorite, lithium imide, lithium iodate, lithium iodide, lithium iridate, lithium iron phosphate, lithium lactate, lithium metaborate, lithium metasilicate, lithium methoxide, lithium molybdate, lithium molybdenum purple bronze, lithium monoxide anion, lithium nickel cobalt aluminum oxides, lithium nickel manganese cobalt oxides, lithium niobate, lithium nitrate, lithium nitride, lithium nitrite, lithium orotate, lithium orthosilicate, lithium oxide, lithium perchlorate, lithium peroxide, lithium platinate, lithium polonide, lithium ruthenate, lithium salicylate, lithium selenide, lithium stearate, lithium succinate, lithium sulfate, lithium sulfide, lithium sulfite, lithium superoxide, lithium tantalate, lithium tetrachloroaluminate, lithium tetrafluoroborate, lithium tetrahydridogallate, lithium tetrakis(pentafluorophenyl)borate, lithium tetramethylpiperidide, lithium titanate, lithium triborate, lithium triethylborohydride, lithium triflate, or lithium tungstate.

7. The method of claim 1, wherein the lithium agent is lithium carbonate.

8. The method of claim 1, wherein the lithium agent is administered through inhalation directly to the nasal passages, paranasal sinuses, nasopharynx, oropharynx, larynx trachea, bronchi, bronchioli, alveolar ducts, alveolar sacs, or alveoli of the subject.

9. The method of claim 1, wherein the lithium agent is co-administered with zinc, a non-steroidal anti-inflammatory agent, an antibiotic, azithromycin, an antiviral medication, a neuraminidase inhibitor, hydroxychloriquine, chloriquine, a histamine-2 receptor antagonist, a steroid, Vitamin C, or oxygen therapy.

10. The method of claim 1, wherein the subject is a human.

11. A kit comprising:
a) a topical form of a lithium agent, the topical form comprising a therapeutically effective amount of the lithium agent for treating a viral infection characterized by a cytokine storm in the respiratory tract of a subject; and
b) zinc, a non-steroidal anti-inflammatory agent, an antibiotic, azithromycin, an antiviral medication, a neuraminidase inhibitor, hydroxychloriquine, chloriquine, a histamine 2 receptor antagonist, a steroid, or Vitamin C.

12. The kit of claim 11, wherein the topical form of the lithium agent is inhalable.

13. The kit of claim 11, further comprising instructions for the use of the topical form of the lithium agent.

14. The kit of claim 12, wherein the viral infection is caused by a virus belonging to the Coronaviridae family.

15. The kit of claim 12, wherein the viral infection is caused by Severe Acute Respiratory Syndrome Coronavirus 2 (SARS-CoV-2) or Human orthopneumovirus.

16. The kit of claim 11, wherein the lithium agent is elemental lithium, lithium acetate, lithium aluminate, lithium aluminum hydride, lithium amide, lithium aspartate, lithium azide, lithium beryllide, lithium bis(trifluoromethanesulfonyl)imide, lithium bis(trimethylsilyl)amide, lithium borate, lithium borohydride, lithium bromide, lithium carbide, lithium carbonate, lithium chlorate, lithium chloride, lithium citrate, lithium cobalt oxide, lithium cyanide, lithium diisopropylamide, lithium disilicate, lithium fluoride, lithium hexafluorogermanate, lithium hexafluorophosphate, lithium hydride, lithium hydroxide, lithium hypochlorite, lithium imide, lithium iodate, lithium iodide, lithium iridate, lithium iron phosphate, lithium lactate, lithium metaborate, lithium metasilicate, lithium methoxide, lithium molybdate, lithium molybdenum purple bronze, lithium monoxide anion, lithium nickel cobalt aluminum oxides, lithium nickel manganese cobalt oxides, lithium niobate, lithium nitrate, lithium nitride, lithium nitrite, lithium orotate, lithium orthosilicate, lithium oxide, lithium perchlorate, lithium peroxide, lithium platinate, lithium polonide, lithium ruthenate, lithium salicylate, lithium selenide, lithium stearate, lithium succinate, lithium sulfate, lithium sulfide, lithium sulfite, lithium superoxide, lithium tantalate, lithium tetrachloroaluminate, lithium tetrafluoroborate, lithium tetrahydridogallate, lithium tetrakis(pentafluorophenyl)borate, lithium tetramethylpiperidide, lithium titanate, lithium triborate, lithium triethylborohydride, lithium triflate, or lithium tungstate.

17. The kit of claim 11, wherein the lithium agent is lithium carbonate.

* * * * *